United States Patent
Drent et al.

(10) Patent No.: US 7,348,454 B2
(45) Date of Patent: Mar. 25, 2008

(54) PROCESS FOR THE HYDROCARBOXYLATION OF ETHYLENICALLY UNSATURATED CARBOXYLIC ACIDS

(75) Inventors: Eit Drent, Amsterdam (NL); Roelof Van Ginkel, Amsterdam (NL); Willem Wabe Jager, Amsterdam (NL)

(73) Assignee: Shell Oil Company, Houston, TX (US)

(*) Notice: Subject to any disclaimer, the term of this patent is extended or adjusted under 35 U.S.C. 154(b) by 265 days.

(21) Appl. No.: 10/557,403

(22) PCT Filed: May 17, 2004

(86) PCT No.: PCT/EP2004/050820

§ 371 (c)(1), (2), (4) Date: Nov. 18, 2005

(87) PCT Pub. No.: WO2004/103942

PCT Pub. Date: Dec. 2, 2004

(65) Prior Publication Data

US 2006/0224015 A1    Oct. 5, 2006

(30) Foreign Application Priority Data

May 22, 2003 (EP) .................................. 03076586

(51) Int. Cl.
*C07C 51/14* (2006.01)
(52) U.S. Cl. ...................................................... 562/517
(58) Field of Classification Search ............... None
See application file for complete search history.

(56) References Cited

U.S. PATENT DOCUMENTS

2001/0044556 A1* 11/2001 Drent et al. ............... 562/550

FOREIGN PATENT DOCUMENTS

WO    01/68583    9/2001
WO    02/48094    6/2002

OTHER PUBLICATIONS

International Search Report dated Oct. 29, 2004 (PCT/EP2004/050820).
Intl Preliminary Report on Patentability (PCT/EP2004/050820).

* cited by examiner

*Primary Examiner*—Paul A. Zucker

(57) ABSTRACT

A process for the hydrocarboxylation of an ethylenically unsaturated carboxylic acid, by reacting it with carbon monoxide and a co-reactant selected from the group of water and carboxylic acids in the presence of a catalyst system including: (a) a source of palladium; (b) a bidentate diphosphine of formula (I), $R^1R^2>P\text{—}R^3\text{—}R\text{—}R^4\text{—}P<R^5R^6$ (I) wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group; (c) a source of anions derived from an acid having a pKa of less than 3, as measured at 18° C. in an aqueous solution.

11 Claims, No Drawings

PROCESS FOR THE HYDROCARBOXYLATION OF ETHYLENICALLY UNSATURATED CARBOXYLIC ACIDS

PRIORITY CLAIM

The present application claims priority to European Patent Application No. 03076568.9 filed 22 May, 2003.

FIELD OF THE INVENTION

This invention relates to a process for the hydrocarboxylation of an ethylenically unsaturated carboxylic acid.

BACKGROUND OF THE INVENTION

In WO2001/68583 there is disclosed a process for the carbonylation of ethylenically unsaturated compounds having 3 or more carbon atoms by reaction with carbon monoxide and an hydroxyl group containing compound in the presence of a catalyst system including:
(a) a source of palladium;
(b) a bidentate diphosphine of formula I,

wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group;
(c) a source of anions derived from an acid having a pKa of less than 3, as measured at 18° C. in an aqueous solution.

The process is carried out in the presence of an aprotic solvent. The preferred hydroxyl containing compounds according to WO2001/68583 are water and alkanols. Notably, the hydrocarboxylation of unsaturated carboxylic acids is not mentioned in this document.

SUMMARY OF THE INVENTION

It has now been found that a process for the hydrocarboxylation of an ethylenically unsaturated carboxylic acid with carbon monoxide and a co-reactant selected from the group of water and carboxylic acids can be very effectively performed in the presence of a catalytic system which differs from that described in WO2001/68583 in that the presence of a separate solvent is only optional. The source of anions is not limited to one having a pKa of less than 3.

Accordingly the present invention provides a process for the hydrocarboxylation of an ethylenically unsaturated carboxylic acid by reacting it with carbon monoxide and a co-reactant selected from the group consisting of water and carboxylic acids, in the presence of a catalyst system which comprises:
(a) a source of palladium;
(b) a bidentate diphosphine of formula I,

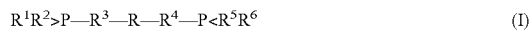

wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group; and
(c) a source of anions derived from an acid.

DETAILED DESCRIPTION OF THE INVENTION

In the process according to the invention, suitable sources for palladium of component (a) include palladium metal and complexes and compounds thereof, such as palladium salts, for example the salts of palladium and halide acids, nitric acid, sulphuric acid or sulphonic acids; palladium complexes, e.g. with carbon monoxide or acetylacetonate, or palladium combined with a solid material such as an ion exchanger. Preferably, a salt of palladium and a carboxylic acid is used, suitably a carboxylic acid with up to 12 carbon atoms, such as salts of acetic acid, propionic acid and butanoic acid, or salts of substituted carboxylic acids such as trichloroacetic acid and trifluoroacetic acid. A very suitable source is palladium(II) acetate.

In the diphosphine of formula I, R represents an optionally substituted aromatic group which is linked to the phosphorus atoms via the alkylene groups. The aromatic group can be a monocyclic group, such as for example a phenyl group or a polycyclic group, such as for example naphthyl, anthryl or indyl group. Preferably, the aromatic group R contains only carbon atoms, but R can also represent an aromatic group wherein a carbon chain is interrupted by one or more hetero atoms, such as nitrogen, sulphur or oxygen atom in for example a pyridine, pyrrole, furan, thiophene, oxazole or thiazole group. Most preferably the aromatic group R represents a phenyl group.

Optionally the aromatic group is substituted. Suitable substituents include groups containing heteroatoms such as halides, sulphur, phosphorus, oxygen and nitrogen. Examples of such groups include chloride, bromide, iodide and groups of the general formula —O—H, —O—$X^2$, —CO—$X^2$, —CO—O—$X^2$, —S—H, —S—$X^2$, —CO—S—$X^2$, —NH$_2$, —NH$X^2$, —N$R^2X^3$, —NO$_2$, —CN, —CO—NH$_2$, —CO—NH$X^2$, —CO—N$X^2X^3$ and —Cl$_3$, in which $X^2$ and $X^3$, independently, represent alkyl groups having from 1 to 4 carbon atoms like methyl, ethyl, propyl, isopropyl and n-butyl. When the aromatic group is substituted it is preferably substituted with one or more aryl, alkyl or cycloalkyl groups, preferably having from 1 to 10 carbon atoms. Suitable groups include, methyl, ethyl, propyl, isopropyl, butyl and iso-butyl, phenyl and cyclohexyl.

Most preferably, however, the aromatic group is non-substituted and only linked to the alkylene groups which connect it with the phosphorus atoms. Preferably the alkylene groups are connected at adjacent positions, for example the 1 and 2 positions, of the aromatic group.

Preferably the alkylene groups are lower alkylene groups. By lower alkylene groups is understood alkylene groups comprising from 1 to 4 carbon atoms. The alkylene groups can be substituted, for example with alkyl groups, or non-substituted. Preferably the alkylene groups are non-substituted. More preferably the alkylene groups are unsubstituted methylene or ethylene groups, most preferably methylene groups.

$R^1$, $R^2$, $R^5$ and $R^6$ can independently represent organic groups containing a tertiary carbon atom through which the group is linked to the phosphorus atom. The groups $R^1$, $R^2$, $R^5$ and $R^6$ are only connected to each other via the phosphorus atom. The organic groups preferably have from 4 to 30 carbon atoms, yet more preferably from 4 to 20 carbon atoms, and again more preferably from 4 to 8 carbon atoms. The tertiary carbon atom can be substituted with aliphatic, cyclo-aliphatic or aromatic substituents or can form part of a substituted saturated or non-saturated aliphatic ring structure. Hence examples of suitable organic groups are tert-butyl, 2-(2-methyl)-butyl, 2-(2-ethyl)butyl, 2-(2-phenyl)butyl, 2-(2-methyl)pentyl, 2-(2-ethyl)pentyl, 2-(2-methyl-4-phenyl)-pentyl, 1-(1-methyl)cyclohexyl and 1-adamantyl groups, and derivatives of these groups, wherein one or more of the carbon atoms are substituted by heteroatoms. Again preferably, the tertiary carbon atom is substituted with alkyl groups, i.e. preferably the organic group is a tertiary alkyl group. Of these, tert-butyl groups and 1-adamantyl groups are most preferred. Preferably the groups $R^1$, $R^2$, $R^5$ and $R^6$ represent the same tertiary alkyl groups, most preferably groups $R^1$, $R^2$, $R^5$ and $R^6$ are tert-butyl groups.

An especially preferred bidentate diphosphine is 1,2-bis [(di(tert-butyl)phosphinomethyl]benzene (also known as bis [di(tert-butyl)phosphino]-o-xylene).

The ratio of moles of bidentate diphosphine, i.e. catalyst component (b), per mole atom of palladium, i.e. catalyst component (a), ranges from 0.5 to 20, preferably from 1 to 10.

Examples of suitable anions, i.e. component (c) of the catalyst system, include anions of phosphoric acid, sulphuric acid, sulphonic acids, carboxylic acids and halogenated carboxylic acids such as trifluoroacetic acid.

Sulphonic acids are in particular preferred, for example trifluoromethanesulphonic acid, p-toluene-sulphonic acid and 2,4,6-trimethylbenzene sulphonic acid, 2-hydroxypropane-2-sulphonic acid, tert-butyl sulphonic acid and methyl sulphonic acid. Especially preferred sulphonic acids are methyl sulphonic acid, tert-butyl sulphonic acid, 2,4,6-trimethylbenzene sulphonic acid. Yet more preferred anions are anions of acids having a pKa of above 3, such as carboxylic acids.

Suitable carboxylic acids are those having from 2-20 carbon atoms, such as acetic acid, propionic acid butyric acid, pentanoic acid and nonanoic acid. Very conveniently the acid corresponding to the unsaturated carboxylic acid reactant can be used as catalyst component (c). In case the reactant is 3-pentenoic acid, this same acid can be conveniently used as the catalyst component (c) as well. The carboxylic acid may also be a mixture of the reactant and its structural isomers. In the case the reactant is 3-pentenoic acid, these include the 2- and 4-pentenoic acid other than the cis-3-pentenoic acid and/or trans-3-pentenoic acid.

Catalyst component (c) can also be an ion exchanging resin containing sulphonic acid groups or carboxylic acid groups.

The molar ratio of the source of anions and palladium, i.e. catalyst components (c) and (b), is suitably between 2:1 and $10^6$:1 and more preferably between 2:1 and $10^5$:1.

The process may optionally be carried out in the presence of a solvent.

The ethylenically unsaturated carboxylic acid has at least 3 carbon atoms. Preferably the ethylenically unsaturated carboxylic acid has from 4 to 20 and more preferably from 4 to 14 carbon atoms, such as acrylic acid, 2-cis-pentenoic acid and/or 2-trans-pentenoic acid or a mixture thereof, 3-cis pentenoic acid and/or 3-trans-pentenoic acid or a mixture thereof 3-pentenoic acid, 4-pentenoic acid, undecenoic acid, cyclopentene carboxylic acid, dicyclopentene carboxylic acid and cyclohexene carboxylic acid. The ethylenically unsaturated carboxylic acid can be substituted or non-substituted.

The co-reactant is water, a carboxylic acid or a combination thereof. Inasmuch as the co-reactant is water, the product obtained will be dibasic carboxylic acid. Mono anhydric carboxylic acids are obtained inasmuch as the co-reactant is a carboxylic acid. Preferably the carboxylic acid co-reactant has the same number of carbon atoms as the ethylenically unsaturated carboxylic acid reactant.

The ratio (v/v) of ethylenically unsaturated carboxylic acid and water can vary between wide limits and suitably lies in the range of 1:0.1 to 1:10, more suitably from 2:1 to 1:2.

The hydrocarboxylation reaction according to the present invention is carried out at moderate temperatures and pressures. Suitable reaction temperatures are in the range of 50-250° C., preferably in the range of 80-150° C. The reaction pressure is usually at least atmospheric. Suitable pressures are in the range of 0.1 to 15 MPa (1 to 150 bar), preferably in the range of 0.5 to 8.5 MPa (5 to 85 bar).

Carbon monoxide partial pressures in the range of 0.1 to 6.5 MPa (1-65 bar) are preferred. In the process according to the present invention, the carbon monoxide can be used in its pure form or diluted with an inert gas such as nitrogen, carbon dioxide or noble gases such as argon.

In the process of the present invention, the addition of limited amounts of hydrogen, such as 3 to 20 mol % of the amount of carbon monoxide used, promotes the hydrocarbonylation reaction. The use of higher amounts of hydrogen, however, tends to cause the undesirable hydrogenation of the ethylenically unsaturated carboxylic acid reactant.

The amount of catalyst used in the process is not critical. Good results are obtained when the amount of palladium is in the range of $10^{-7}$ to $10^{-1}$ gram atom per mole of ethylenically unsaturated compound. Preferably this amount is in the range of $10^{-5}$ to $5 \times 10^{-2}$ gram atom per mole.

The invention will be illustrated by the following examples.

EXAMPLES 1-3

Hydrocarboxylation of 3-pentenoic Acid to Adipic Acid

A 250 ml stirred autoclave, made of HASTELLOY C, was charged with 40 ml diglyme (diethylene glycol dimethyl ether), 5 ml water and 15 ml 3-pentenoic acid (HASTELLOY C is a trademark). Then a solution of the preformed catalyst composition of 0.1 mol palladium acetate, 0.5 mol of the ligand and 1 mol methane sulphonic acid in 10 ml of acetone was added and the autoclave was closed and evacuated.

The ligand in Examples 1-3 was 1,2-bis[di(tert-butyl) phosphinomethyl]benzene and in Comparative Example A it was 1,3-bis(di-tert-butylphosphino)propane.

The autoclave was pressurized with CO to 3 MPa and heated at 90 or 105° C. for 10 hr.

After reaction the autoclave was cooled and opened. The contents consisted of a slurry of adipic acid, diglyme and pentenoic acid.

The initial carbonylation rate (mol per mol Pd per hour) of this batch operation, as presented in Table I, is defined for Examples 1-3 as the mean rate of carbon monoxide consumption (pressure drop) over the first 30% substrate consumption. For Comparative Example A, which did not reach 40% substrate consumption, the initial carbonylation rate is defined as the mean rate of CO consumption over the first two hours.

TABLE I

| Example | Temp. °C. | Rate mol/mol Pd/hr |
|---|---|---|
| 1 | 105 | 270 |
| 2 | 90 | 330 |
| 3 | 105 | 330 |
| A | 100 | 10 |

The liquid phase of the slurry of Examples 2 and 3 was analysed with GlC, and showed a pentenoic acid conversion to adipic acid of more than 90 mol % in both cases. Also, 15 g and 17 g respectively of white adipic acid was recovered by filtration at room temperature. Analysis by $^1$H NMR in d-DMSO showed more than 99% purity of adipic acid in both cases.

The slurry of Comparative Example A was analysed in the same way and showed a pentenoic acid conversion of 5 mol % and a purity of 60% adipic acid.

EXAMPLES 4-7

Hydrocarboxylation of 3-pentenoic Acid Out of a Mixture to Adipic Acid

A mixed substrate of the following composition was used:

| | |
|---|---|
| butenyl esters of pentenoic acid | 6.1 wt % |
| butenyl esters of nonanoic acid | 1.4 wt % |
| cis/trans 3-pentenoic acid | 84.0 wt % |
| 2- and 4-pentenoic acid | 1.4 wt % |
| nonanoic acid | 6.9 wt % |

Four batches of 30 ml each of this mixed substrate were reacted with CO and water as follows.

A 250 ml magnetically stirred autoclave, made of HAS-TELLOY C, was charged with water as specified in Table II below and with 30 ml of the distilled product of Example 13. Then 0.1 mol palladium acetate and 0.5 mol of the ligand 1,2-Bis(di-tert-butylphosphinomethyl)benzene were added and the autoclave closed and evacuated. The autoclave was pressurized with $H_2$ and/or CO to partial pressures as indicated in Table III, sealed, heated to 135° C. and maintained at that temperature for 15 hours. Finally the autoclave was cooled and the reaction mixture was analysed with GLC.

The reaction mixture was almost completely composed of solid adipic acid. THF was added to form a slurry of adipic acid in THF. The THF phase was analysed by GLC and the conversion of pentenoic acid was determined from the residual pentenoic acid. In all experiments pentenoic acid conversion was higher than 90%. Selectivity to adipic acid was >95%.

The initial carbonylation rate (mol per mol of Pd per hour) of this batch operation, as presented in Table II, is defined as the mean rate of carbon monoxide consumption (pressure drop) over the first 30% substrate consumption.

TABLE II

| Example | Water charge | Induction time (hr)** | $H_2$ partial pressure MPa | CO partial pressure MPa | Initial carbonylation rate mol/mol Pd/hr |
|---|---|---|---|---|---|
| 4 | 5 ml | 6 | 10 | 40 | 610 |
| 5 | 5 ml | 5 | — | 60 | 700 |
| 6 | 7 ml | 10 | — | 65 | 730 |
| 7 | 2 + 5 ml* | <1 | — | 65 | 880 |

*5 ml were added after 1 hr reaction
**The induction time is caused by the butenyl pentenoic acid esters present in the feed (6.1 wt % according to Table II), which here were initially converted to pentenoic acid and butadiene. At the low initial water concentration of Example 7 this pentenoate conversion was rapidly achieved.

We claim:

1. A process for the hydrocarboxylation of an ethylenically unsaturated carboxylic acid by reacting it with carbon monoxide and a co-reactant selected from the group consisting of water and carboxylic acids in the presence of a catalyst system which consists of:
   (a) a source of palladium;
   (b) a bidentate diphosphine of formula I, $$R^1R^2 > P-R^3-R-R^4-P < R^5R^6 \qquad (I)$$

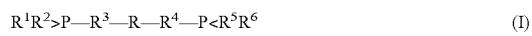

wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group; and
   (c) a source of anions derived from an acid having a pKa of above 3.

2. The process of claim 1 wherein R is a phenyl group.

3. The process of claim 1 wherein $R^3$ and $R^4$ are methylene groups.

4. The process of claim 1 wherein $R^1$, $R^2$, $R^5$ and $R^6$ are tert-butyl groups.

5. The process of claim 1 wherein the source of anions is derived from the acid corresponding to the unsaturated acid carboxylic acid reactant.

6. The process of claim 1 wherein the source of anions is derived from a carboxylic acid.

7. The process of claim 1 wherein the reaction temperature is in the range of 50° C. to 250° C., the reaction pressure is in the range of 0.1 to 15 MPa, and the carbon monoxide partial pressure is in the range of 0.1 to 6.5 MPa.

8. The process of claims 1 wherein an amount of 3 to 20 mol %, related to the carbon monoxide, of hydrogen is added.

9. The process of claims 1 wherein the ethylenically unsaturated carboxylic acid has from 4 to 20 carbon atoms.

10. The process of claim 9 wherein the ethylenically unsaturated carboxylic acid is pentenoic acid.

11. The process of claim 1 wherein the source of anions is an ion exchanging resin containing carboxylic acid groups.

* * * * *